(12) United States Patent
O'Phelan et al.

(10) Patent No.: US 6,275,729 B1
(45) Date of Patent: *Aug. 14, 2001

(54) SMALLER ELECTROLYTIC CAPACITORS FOR IMPLANTABLE DEFIBRILLATORS

(75) Inventors: Michael J. O'Phelan, Oakdale; James M. Poplett, Golden Valley; Robert R. Tong, Fridley; Alexander Gordon Barr, Burnsville, all of MN (US)

(73) Assignee: Cardiac Pacemakers, Inc., St. Paul, MN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/165,848

(22) Filed: Oct. 2, 1998

(51) Int. Cl.[7] .................. A61N 1/39; H01G 9/00
(52) U.S. Cl. .................. 607/5; 29/25.03
(58) Field of Search .................. 607/5; 29/25.03

(56) References Cited

U.S. PATENT DOCUMENTS

| 3,398,333 | 8/1968 | Zeppieri ..................... 317/230 |
| 3,555,369 | 1/1971 | Yoshino et al. . |

(List continued on next page.)

FOREIGN PATENT DOCUMENTS

| 0753868 | 1/1997 | (EP) | ............... H01G/9/012 |
| 0851446 | 7/1998 | (EP) | ............... H01G/9/055 |
| 99/51301 | 10/1999 | (WO) | ............... A61N/1/375 |
| 99/51302 | 10/1999 | (WO) | ............... A61N/1/375 |
| 99/51303 | 10/1999 | (WO) | ............... A61N/1/39 |
| 99/66985 | 12/1999 | (WO) | ............... A61N/1/39 |

OTHER PUBLICATIONS

Database WPI Abstract, XP–002126511, An–1997–031410 (03), Publication No. JP 08293430, Derwent Publications Ltd., London, GB, 1 p., (Nov. 5, 1996).
Patent Abstracts of Japan, 15 (40), Publication No. 02276222 (U. Noriki), 1 p., (Nov. 13, 1990).
Patent Abstracts of Japan, 16 (134), Publication No. 03296207 (K. Kaname), 1 p., (Dec. 26, 1991).
Patent Abstracts of Japan, 16 (291), Publication No. 04074409 (A. Akiyoshi), 1 p., (Jul. 16, 1990).

(List continued on next page.)

Primary Examiner—Carl H. Layno
(74) Attorney, Agent, or Firm—Schwegman, Lundberg, Woessner & Kluth, P.A.; Eduardo E. Drake (57) ABSTRACT

Implantable defibrillators are implanted into the chests of patients prone to suffering ventricular fibrillation, a potentially fatal heart condition. A critical component in these devices is an aluminum electrolytic capacitors, which stores and delivers one or more life-saving bursts of electric charge to a fibrillating heart. These capacitors make up about one third the total size of the defibrillators. Unfortunately, conventional manufacturers of these capacitors have paid little or no attention to reducing the size of these capacitors through improved capacitor packaging. Accordingly, the inventors contravened several conventional manufacturing principles and practices to devise unique space-saving packaging that allows dramatic size reduction. One embodiment of the invention uses thinner and narrower separators and top and bottom insulative inserts to achieve a 330-volt operating, 390-volt surge, 190-microfarad, 30-Joule aluminum electrolytic capacitor which is 33 percent smaller than conventional capacitors having similar electrical traits.

23 Claims, 6 Drawing Sheets

U.S. PATENT DOCUMENTS

| | | | |
|---|---|---|---|
| 3,659,615 | 5/1972 | Enger | 128/419 P |
| 3,765,956 | 10/1973 | Li | 148/33 |
| 3,789,502 | 2/1974 | Callins et al. | 29/570 |
| 3,918,460 | 11/1975 | King et al. | 128/419 P |
| 3,943,937 | 3/1976 | King et al. | 128/419 P |
| 4,041,955 | 8/1977 | Kelly et al. | 128/419 P |
| 4,041,956 | 8/1977 | Purdy et al. | 128/419 P |
| 4,136,435 | 1/1979 | Li | 29/572 |
| 4,183,600 | 1/1980 | Schroeder | 339/218 R |
| 4,243,042 | 1/1981 | Ware | 128/419 P |
| 4,333,469 | 6/1982 | Jeffcoat et al. | 128/419 F |
| 4,371,406 | 2/1983 | Li | 148/171 |
| 4,385,342 | 5/1983 | Puppolo et al. | 361/433 |
| 4,395,305 | 7/1983 | Whitman | 156/665 |
| 4,521,830 | 6/1985 | Aultman et al. | 361/433 |
| 4,546,415 | 10/1985 | Kent et al. | 361/433 |
| 4,663,824 | 5/1987 | Kenmochi | 29/570 |
| 4,690,714 | 9/1987 | Li | 437/208 |
| 4,692,147 | 9/1987 | Duggan | 604/93 |
| 4,771,362 | 9/1988 | Behn | 361/306 |
| 4,782,235 | 11/1988 | Lejeune et al. | 250/423 R |
| 4,907,130 | 3/1990 | Boulloy et al. | 361/529 |
| 4,942,501 * | 7/1990 | MacFarlane et al. | 361/523 |
| 4,944,300 | 7/1990 | Saksena | 128/419 D |
| 4,987,519 | 1/1991 | Hutchins et al. | 361/518 |
| 5,055,889 | 10/1991 | Beall | 357/14 |
| 5,055,975 | 10/1991 | Behrend . | |
| 5,086,374 | 2/1992 | MacFarlane et al. | 361/525 |
| 5,131,388 | 7/1992 | Pless et al. | 128/419 D |
| 5,146,391 | 9/1992 | MacFarlane et al. | 361/525 |
| 5,153,820 | 10/1992 | MacFarlane et al. | 361/525 |
| 5,245,499 | 9/1993 | Senes | 361/56 |
| 5,275,621 | 1/1994 | Mehra . | |
| 5,324,910 | 6/1994 | Isawa | 219/118 |
| 5,370,663 | 12/1994 | Lin | 607/5 |
| 5,380,341 | 1/1995 | Matthews et al. | 29/25.03 |
| 5,439,760 | 8/1995 | Howard et al. | 429/94 |
| 5,456,698 | 10/1995 | Byland et al. | 607/36 |
| 5,468,984 | 11/1995 | Efland et al. | 257/356 |
| 5,500,534 | 3/1996 | Robinson et al. | 250/385.1 |
| 5,522,851 | 6/1996 | Fayram | 607/5 |
| 5,536,960 | 7/1996 | Hayaski | 257/369 |
| 5,536,964 | 7/1996 | Green et al. | 257/432 |
| 5,545,184 | 8/1996 | Dougherty | 607/5 |
| 5,584,890 | 12/1996 | MacFarlane et al. | 29/25.03 |
| 5,591,211 | 1/1997 | Meltzer | 607/5 |
| 5,597,658 | 1/1997 | Kejha | 429/94 |
| 5,628,801 | 5/1997 | MacFarlane et al. | 29/25.03 |
| 5,642,252 | 6/1997 | Sakamoto et al. | 361/93 |
| 5,660,737 | 8/1997 | Elias et al. | 216/6 |
| 5,661,625 | 8/1997 | Yang | 361/92 |
| 5,661,629 | 8/1997 | MacFarlane et al. | 361/505 |
| 5,674,260 | 10/1997 | Weinberg | 607/36 |
| 5,677,539 | 10/1997 | Apotovsky et al. | 250/370.13 |
| 5,688,698 | 11/1997 | Robinson et al. | 437/3 |
| 5,697,953 | 12/1997 | Kroll et al. | 607/5 |
| 5,698,453 | 12/1997 | Green et al. | 437/3 |
| 5,711,861 | 1/1998 | Ward et al. | 204/403 |
| 5,711,988 | 1/1998 | Tsai et al. | 427/80 |
| 5,728,594 | 3/1998 | Efland et al. | 437/40 |
| 5,748,439 | 5/1998 | MacFarlane et al. | 361/525 |
| 5,776,628 | 7/1998 | Kraft et al. | 429/94 |
| 5,800,857 | 9/1998 | Ahmad et al. | 427/80 |
| 5,808,857 | 9/1998 | Stevens | 361/503 |
| 5,814,082 | 9/1998 | Fayram et al. | 607/5 |
| 5,837,995 | 11/1998 | Chow et al. | 250/214 LS |
| 5,859,456 | 1/1999 | Efland et al. | 257/335 |
| 5,867,363 | 2/1999 | Tsai et al. | 361/502 |
| 5,895,416 | 4/1999 | Barreras, Sr. et al. | 607/62 |
| 5,895,733 | 4/1999 | Chespi et al. | 429/219 |
| 5,904,514 | 5/1999 | Konuma et al. | 438/165 |
| 5,926,357 | 7/1999 | Elias et al. | 361/302 |
| 5,930,109 | 7/1999 | Fishler | 361/508 |
| 5,949,638 | 9/1999 | Greenwood et al. | 361/508 |
| 5,959,535 | 9/1999 | Remsburg | 340/604 |
| 5,963,418 | 10/1999 | Greenwood, Jr. et al. | 361/508 |
| 5,968,210 | 10/1999 | Strange et al. | 29/25.03 |
| 5,980,977 | 11/1999 | Deng et al. | 427/79 |
| 5,983,472 | 11/1999 | Fayram et al. | 29/25.42 |
| 6,006,133 | 12/1999 | Lessar et al. | 607/5 |
| 6,009,348 | 12/1999 | Rorvick et al. | 607/5 |

OTHER PUBLICATIONS

Patent Abstracts of Japan, 18 (3), Publication No. 05251283 (T. Fumiyasu), 1 p., (Sep. 28, 1993).

Patent Abstracts of Japan, 1996 (6), Publication No. 08055762 (E. Akira), 1 p., (Feb. 27, 1996).

Patent Abstracts of Japan, 97 (12), Publication No. 09219343 (I. Toshihiko), 1 p., (Aug. 19, 1997).

Lunsman, P., et al., "High Energy Density Capacitors for Implantable Defibrillators", *Proceedings of the 16th Capacitor and Resistor Technology Symposium*, Monteleone Hotel, New Orleans, Louisiana, pp. 277–280, (Mar. 11–15, 1996).

Moynihan, J.D., et al., *Theory, Design and Application of Electrolytic Capacitors*, Copyright by John D. Moynihan, 136 p., (1982).

"Understanding Aluminum Electrolytic Capacitors", *United Chemi–Con*, 7 p., (Date Unknown).

Jenkins, et al., "Diagnosis of Atrial Fibrillation Using Electrogram from Chronic Leads: Evaluation of Computer Algorithm", *PACE*, 11, pp. 622–631, (1988).

Morris, et al., "Intracardiac Electrogram Transformation: Morphometric Implications for Implantable Devices", *Journal of Electrocardiology*, 29 Supplement, pp. 124–129, (1996).

Schuller, et al., "Far Field R–Wave Sensing—An Old Problem Reappearing", *PACE*, 19, Part II, NASPE Abstract No. 264, p. 631, (1996), Stephany, et al., "Real–Time Estimation of Magnitude–Square Coherence for Use in Implantable Devices", *IEEE Computers in Cardiology*, pp. 375–378, (1992).

* cited by examiner

SMALLER ELECTROLYTIC CAPACITORS FOR IMPLANTABLE DEFIBRILLATORS

BACKGROUND OF THE INVENTION

The present invention concerns electrolytic capacitors, particularly those for use in medical devices, such as implantable defibrillators.

Every year more than half a million people in the United States suffer from heart attacks, more precisely cardiac arrests. Many of these cardiac arrests stem from the heart chaotically twitching, or fibrillating, and thus failing to rhythmically expand and contract as necessary to pump blood. Fibrillation can cause complete loss of cardiac function and death within minutes. To restore normal heart contraction and expansion, paramedics and other medical workers use a device, called a defibrillator, to electrically shock a fibrillating heart.

Since the early 1980s, thousands of patients prone to fibrillation episodes have had miniature defibrillators implanted in their bodies, typically in the left breast region above the heart. These implantable defibrillators detect onset of fibrillation and automatically shock the heart, restoring normal heart function without human intervention. A typical implantable defibrillator includes a set of electrical leads, which extend from a sealed housing into the heart of a patient after implantation. Within the housing are a battery for supplying power, heart-monitoring circuitry for detecting fibrillation, and a capacitor for storing and delivering a burst of electric charge through the leads to the heart.

The capacitor is typically an aluminum electrolytic capacitor, which includes two long strips of aluminum foil with two long strips of paper, known as separators, in between them. One of the aluminum foils serves as a cathode (negative) foil, and the other serves as an anode (positive) foil. Each foil has an aluminum tab, extending from its top edge, to facilitate electrical connection to other parts of the capacitor.

The foil-and-paper assembly, known as the active element, is rolled around a removable spindle or mandrel to form a cylinder and placed in a round tubular case, with the two tabs extending toward the top of the case. The paper is soaked, or impregnated, with a liquid electrolyte—a very electrically conductive solution containing positive or negative ions. And, the tubular case is sealed shut with a lid called a header. Extending from the header are two terminals connected respectively to the anode foil and cathode foil via the aluminum tabs.

In recent years, manufacturers of aluminum electrolytic capacitors have focused almost single-mindedly on improving the active element by developing aluminum foils, electrolytes, and multiple-anode arrangements that improve capacitor performance, specifically energy density—the amount of energy or charge a capacitor stores per unit volume. For example, because energy density is directly proportional to the surface area of the aluminum foil making up the capacitive element, manufacturers have focused on methods of etching microscopic hills and valleys into foils to increase their effective surface area.

In comparison, capacitor manufacturers have made little, if any, effort to improve packaging of the active element. For example, three leading manufactures of electrolytic capacitors—Rubycon, United Chemicon, and Roederstein—presently provide 330–360 volt, dual-anode aluminum electrolytic capacitors which have total volumes greater than about 6.5 cubic-centimeters (which is roughly the same size as a AA battery.) Yet, when the present inventors studied how this space was used, they determined that the ratio of the volume of the active element to the overall volume of these capacitors was only about 40 percent. Thus, the inventors concluded that about 60 percent of the total capacitor volume was wasted in the sense of failing to directly contribute to the performance of these electrolytic capacitors.

Accordingly, the inventors identified an unmet need to reduce the size of electrolytic capacitors, especially those intended for implantable defibrillators, through better packaging.

SUMMARY OF THE INVENTION

To address this and other needs, the inventors devised several improvements intended to reduce the overall size of electrolytic capacitors, particularly those intended for implantable defibrillators. With these improvements, the inventors built an exemplary 360-volt operating, 390-volt surge, 190-microfarad, 15.9-Joule aluminum electrolytic capacitor about 33 percent smaller than conventional capacitors with comparable electrical traits.

One improvement contributing to this size reduction is the use of one or more separators having a thickness less than the standard one-thousandth of an inch used in conventional electrolytic capacitors. The exemplary embodiment uses combinations of paper separators with thicknesses of 0.000787, 0.0005, and 0.00025 inches. For conventional cylindrically wound active elements, reducing separator thickness reduces the space necessary to contain the separators. In turn, this allows one to reduce the diameter and volume of the active element and thus the total volume of the capacitor, or alternatively to increase the size of other components of the active element to increase energy density for a given total volume.

In devising this improvement, the inventors recognized that the conventional practice of using thick paper separators stems from at least three design objectives that are of lesser relevance to implantable defibrillators. The first is that thicker paper reduces electrolyte depletion, or evaporation, and thus generally increases capacitor life. However, the inventors determined that electrolyte depletion has much less effect on capacitor life in medical device applications than it does in the typical applications that govern how conventional electrolytic capacitors are built. In particular, implanted defibrillators are generally not subject to the same long-term temperature variations and extremes that conventional capacitors are designed to withstand.

Secondly, conventional manufacturers used the standard thick paper because it is less likely to tear or break during fabrication, particularly during the conventional high-speed process of winding the foil-and-paper assembly around a spindle. Thus, using the thick paper allows conventional manufacturers to make capacitors faster. However, manufacturing speed is not very important to defibrillator makers who need to make many fewer capacitors than conventional manufacturers and thus can generally afford more time making them.

Thirdly, conventional manufacturers use the thick papers to reduce the chance of anode and cathode foils contacting each other and therefore causing capacitor failure during functional testing. Since failed capacitors are generally discarded or recycled, using thick papers ultimately reduces manufacturing waste. However, waste is of less concern when making a small number of capacitors for implantable defibrillators than it is when making millions of capacitors as do most conventional manufacturers.

Another improvement contributing to the 33-percent size reduction is the use of separators with end margins less than two millimeters. The end margins are the portions of the separators which extend beyond the width of the cathode and anode foils. Conventional paper separators are about four-to-six millimeters wider than the aluminum foils of the active element, with the excess width typically divided to form equal top and bottom margins of two-to-three millimeters. Thus, when wound into a roll and stood up on one end, the top and bottom margins increase the overall height of the active element and the overall height of the case needed to contain the active element.

Conventional manufacturers use the large end margins for at least two reasons: to protect the foils from damage during high-speed manufacturing processes, and to insulate the foils of the active element from an aluminum case after insertion into the case. In particular, during high-speed winding, the foil and paper can easily become misaligned or skewed so that the edges of the foil extend beyond the edges of the papers, making them prone to bending, creasing, or tearing. The large, conventional end margins allow room for misalignment while also protecting the foil edges during high-speed winding. After insertion into a tubular case, the end margins separate the edges of the rolled foil from the top and bottom of the case, preventing the electrically conductive case from shorting the anode and cathode foils.

In devising this improvement, the inventors determined that the end margins could be greatly reduced, even eliminated completely in some embodiments, by more carefully winding the foils and separators during manufacture. Additionally, the inventors devised other ways of insulating foils from cases, while reducing capacitor size.

Specifically, the exemplary embodiment of the invention, which has little or no end margins, includes insulative inserts, for example, flat paper disks, between the bottom of the active element and the bottom of the case and between the top of the active element and the underside of a lid on the case. Other embodiments enclose substantially all of the active element within an insulative bag.

Other improvements include reducing the thickness of the capacitor lid, or header, by about 50 percent, reducing the space between the underside of the lid and the top of the active element, reducing the diameter of the normally empty mandrel region of the active element, and reducing thickness of the aluminum tube. Like the use of thinner separators, smaller end margins, and insulative inserts, these ultimately allow reductions in the size of electrolytic capacitors and implantable defibrillators which incorporate them.

DESCRIPTION OF THE PREFERRED EMBODIMENTS

The following detailed description, which references and incorporates FIGS. 1–6, describes and illustrates one or more specific embodiments of the invention. These embodiments, offered not to limit but only to exemplify and teach, are shown and described in sufficient detail to enable those skilled in the art to implement or practice the invention. Thus, where appropriate to avoid obscuring the invention, the description may omit certain information known to those of skill in the art.

Figure 1:
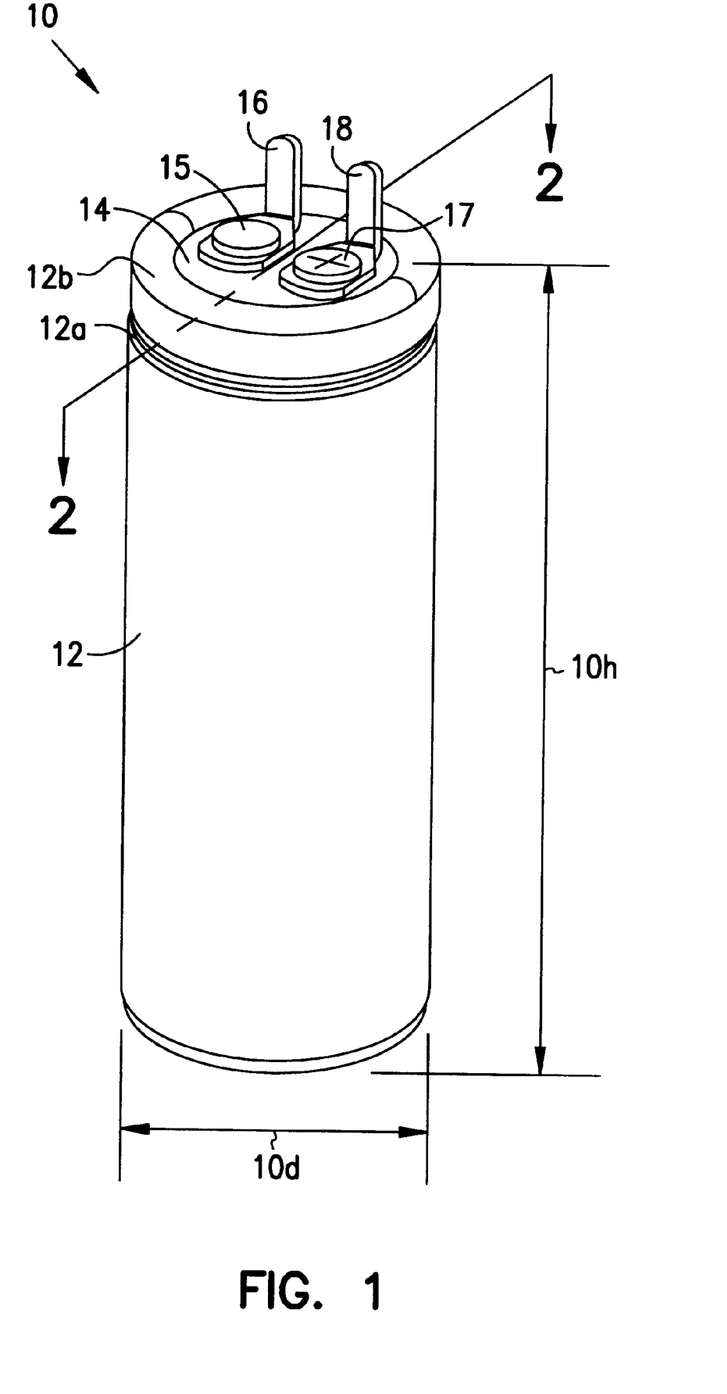
FIG. 1 is a perspective view of an exemplary aluminum electrolytic capacitor 10 incorporating various space-saving features to achieve a 33-percent size reduction over conventional electrolytic capacitors.

FIG. 1 shows a perspective view of an exemplary 360-volt operating, 390-volt surge, 190-microfarad, 15.9-Joule (stored) electrolytic capacitor 10 which incorporates various space-saving features of the present invention. Capacitor 10 has a diameter 10$d$ of about 14.5 millimeters and a total height 10$h$ of about 30 millimeters, and a total volume of about five cubic-centimeters. Thus, capacitor 10 has an energy density of about 3.2 Joules per cubic-centimeter.

In contrast, conventional electrolytic capacitors with comparable electrical characteristics and of about the same diameter have heights greater than or equal to about 40 millimeters and total volumes greater than or equal to about 6.6 cubic-centimeters, with energy densities around 2.4 Joules per cubic-centimeter. Thus, the exemplary capacitor is about 33 percent smaller than conventional capacitors with similar electrical traits.

More specifically, capacitor 10 includes a cylindrical aluminum case 12, a header (or lid) 14, and two aluminum terminals 16 and 18. Two rivets 15 and 17 fasten terminals 16 and 18 to header 14. Aluminum case 12, which houses an active element 20 (not visible in this view), includes a circumferential seating groove 12$a$ and a rolled lip 12$b$, both of which secure header 14 to case 12.

Figure 2:
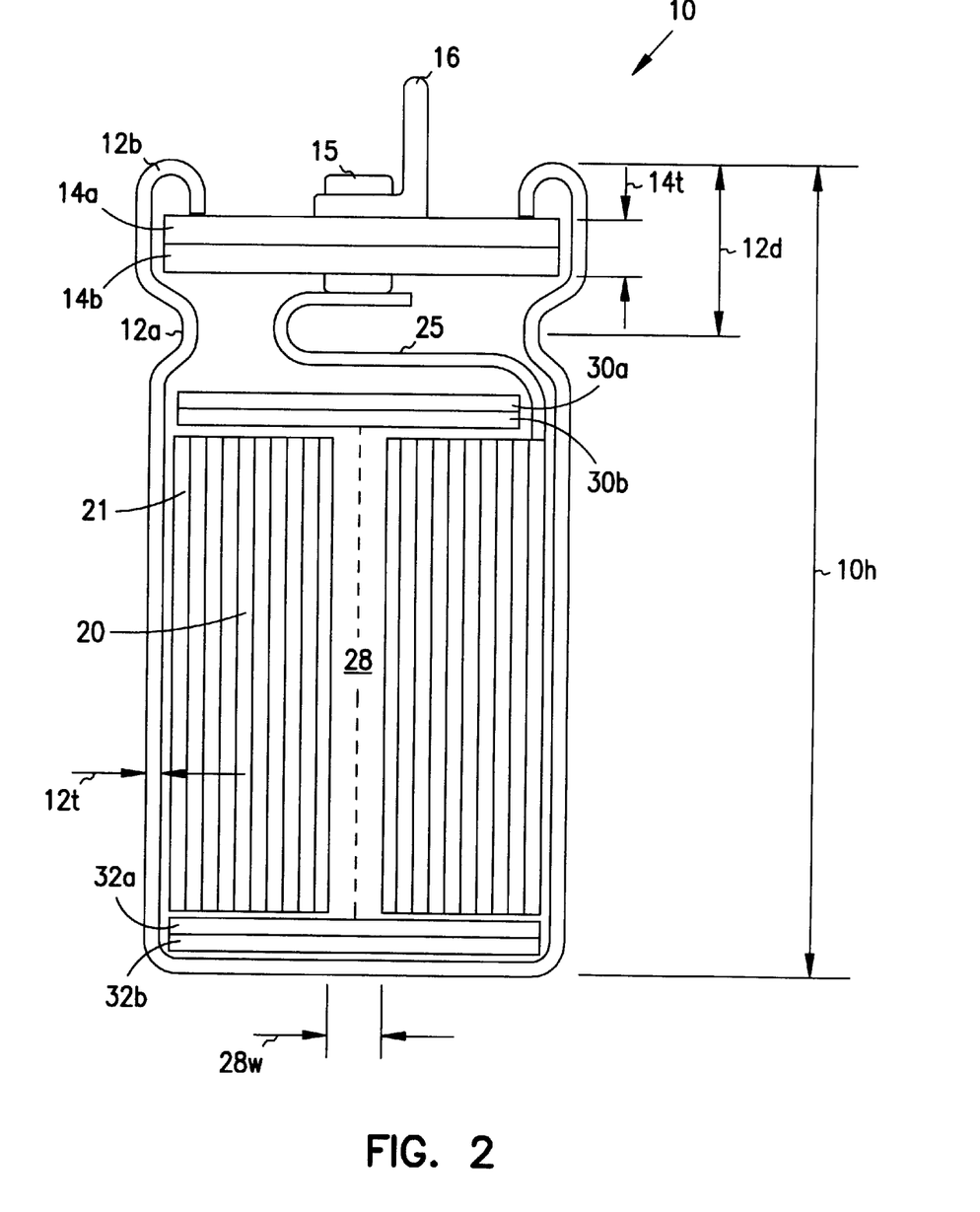
FIG. 2 is a cross-sectional view of electrolytic capacitor 10 taken along line 2—2 of FIG. 1.

FIG. 2, a cross-section taken along line 2—2 in FIG. 1, shows that case 12 has a thickness 12$t$ and that groove 12$a$ is spaced a distance 12$d$ from lip 12$b$. In the exemplary embodiment, thickness 12$t$ is about 0.010 inches, and distance 12$d$ is about 0.145 inches. Additionally, groove 12$a$ has a radius of about 0.035 inches, and lip 12$b$, which is formed by rolling over the top edge of case 12, has a radius of about 0.015 inches. Groove 12$a$ and lip 12$b$ each have a smaller radius than the corresponding features of conventional capacitors. In another embodiment, case 12 is vertically compressed to completely flatten or reduce the height of groove 12$a$ and thus to further reduce the height and volume of capacitor 10.

FIG. 2 also shows that header 14 comprises two bonded layers 14$a$ and 14$b$ and has a total thickness 14$t$. Layer 14$a$ consists of rubber, and layer 14$b$ consists of a phenolic resin. Although thickness 14$t$ is about two millimeter in the exemplary embodiment, it ranges inclusively between 0.5 to 2 millimeters in other embodiments. In contrast, conventional aluminum electrolytic capacitors use headers that are about three to four millimeters thick.

FIG. 2 also shows that capacitor 10 includes an active element 20 comprising about 19 turns of a layered capacitive assembly 21 around mandrel region 28 and two pairs of insulative inserts 30$a$–30$b$ and 32$a$–32$b$ separating the top and bottom of active element 20 from interior surfaces of case 12. For clarity, FIG. 2 omits a plastic insulative sheath that surrounds the vertical surfaces of active element 20. In the exemplary embodiment, this sheath is a piece of transparent tape having a width of 1.125 inches (or 28.6 millimeters).

Figure 3:
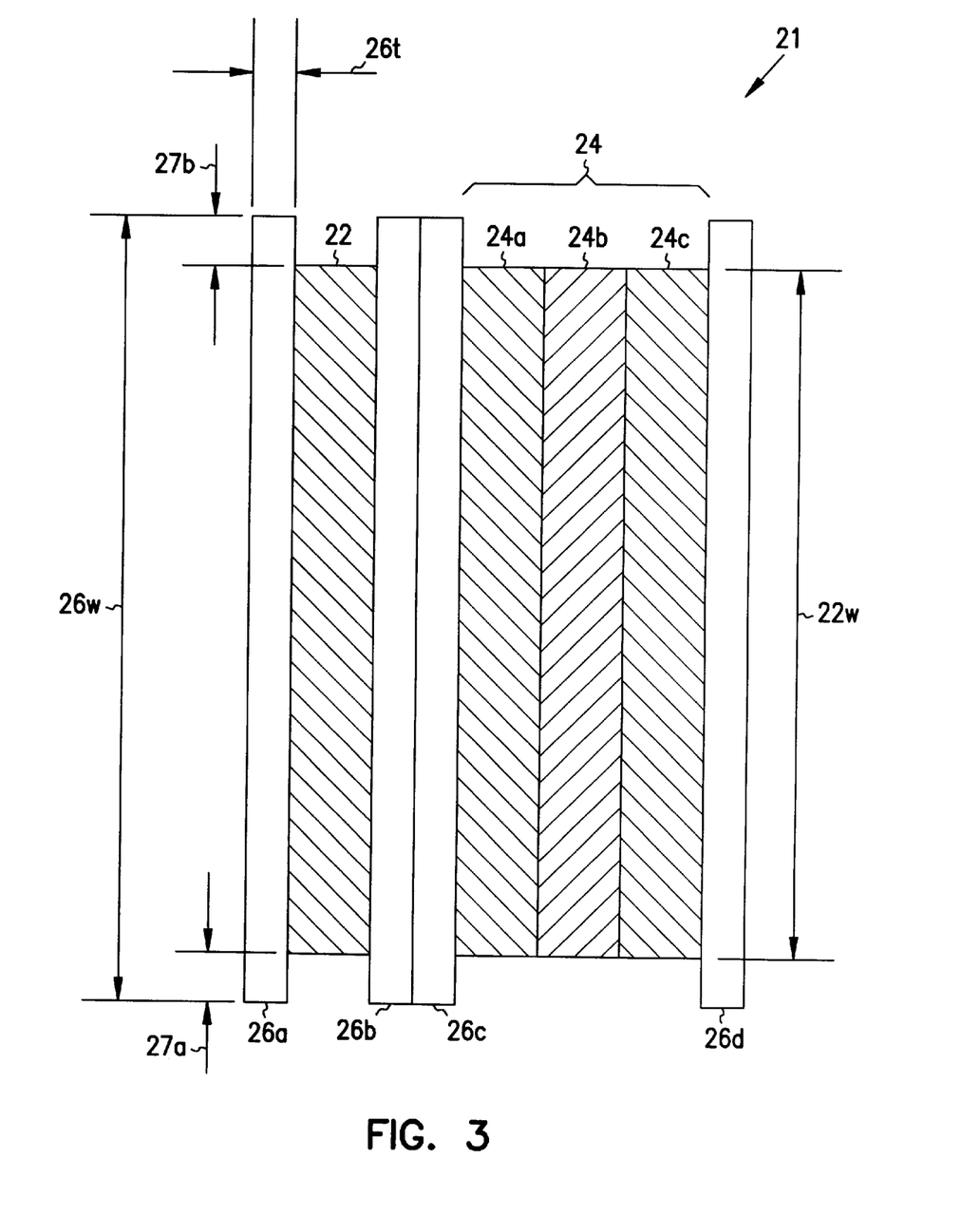
FIG. 3 is a cross-sectional view of a layered capacitive assembly 21 used to form active element 20 of FIG. 2.

FIG. 3, a cross sectional view of layered capacitive assembly 21, shows that it includes a cathode 22, a three-foil anode 24, and four electrolyte-impregnated separators 26a, 26b, 26c, and 26d. Cathode 22 and anode 24 each have a width (or height) 22w, which partly determines a minimum height of case 12. Though not shown in FIG. 3 for clarity, cathode 22 and anode 24 also include insulative or dielectric coatings, for example aluminum or tantalum oxide, on at least their facing surfaces. In this exemplary embodiment, cathode 22 and three constituent foils 24a, 24b, and 24c of anode 24 are about 24 millimeters wide and 100 micrometers thick. Cathode 22 is about 422 millimeters long and anode 24 is about 410 millimeters long.

Although not shown in FIG. 3, anode foils 24a, 24b, and 24c are connected to a single aluminum anode tab 25 (which is shown in FIG. 2). Alternatively, individual anode tabs can be connected to each anode members, and to each other to form a joint or composite anode tab. For more details on these or other types of tabs incorporated in other embodiments of the invention, see co-pending U.S. Pat. applications 09/063692, filed on Apr. 21, 1998, and 09/076023, filed on May 11, 1998, now issued as U.S. Pat. No. 6,110,233, which are respectively entitled Electrolytic Capacitor and Multi-Anodic Attachment and Wound Multi-Anode Electrolytic Capacitor with Offset Anodes and which are incorporated herein by reference.

Anode tab 25, shown in FIG. 2, is ultrasonically welded to rivet 15 and thus electrically connected to terminal 16. In this embodiment, anode tab 25 is folded over itself; however, other embodiments omit this fold to reduce the space between header 14 and the top of active element 20. Though not visible in FIG. 2 or FIG. 3, cathode 22 includes a cathode tab which is similarly connected via rivet 17 to terminal 18.

Figure 4:
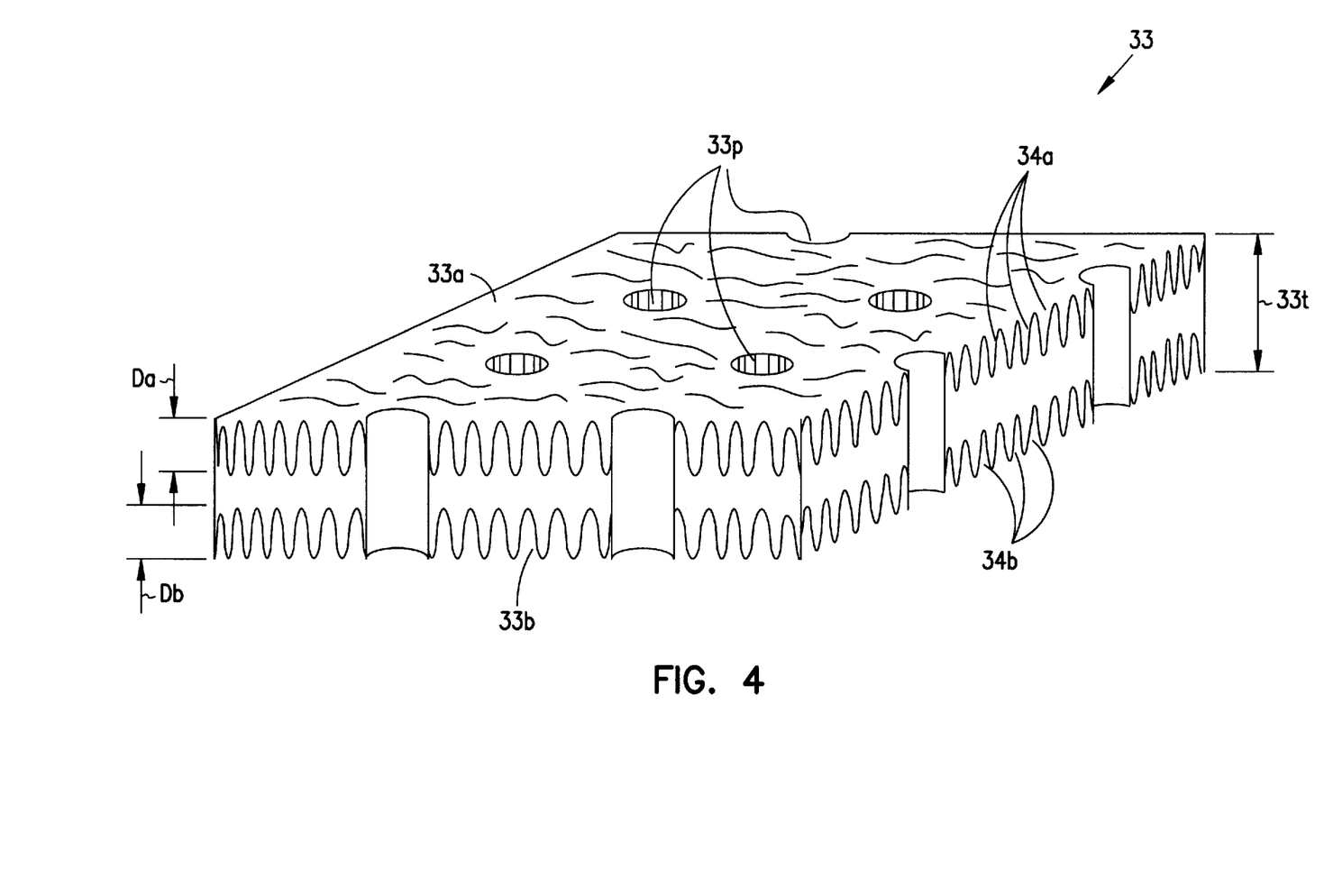
FIG. 4 is a perspective view of a unique foil structure 33 included within some alternative embodiments of capacitive assembly 21.

Cathode 22 and anode foils 24a, 24b, and 24c are made of an electrically conductive material, such as aluminum or tantalum foil, with the anode etched to enhance its effective surface area. Examples of suitable etched foil structures include conventional core-etched and tunnel-etched foils, and a novel perforated-core-etched foil as well as various combinations of these foils. For instance, one embodiment forms anode 24 by stacking a core-etched or tunnel-etched foil with two perforated-core-etched foils. FIG. 4 shows an example of a perforated-core-etched foil 33.

Foil 33 includes two opposing surfaces 33a and 33b that define an average foil thickness 33t and a number of perforations, or holes, 33p that extend all the way through the foil. Surfaces 33a and 33b include respective sets of surface cavities 34a and 34b, which have respective average maximum depths Da and Db and respective average cross-sectional areas Sa and Sb (measured in a plane generally parallel to the foil). In the exemplary embodiment, the perforations, which are formed using laser, etch, or mechanical means, have an average cross-sectional area that is 2-100 times larger than the average cross-sectional areas of the cavities. Depths Da and depths Db are approximately equal to one third or one quarter of thickness 33t, and cross-sectional areas Sa and Sb are equal and range inclusively between about 0.16 and 0.36 square-microns. The layout or arrangement of perforations can take any number of forms, including, for example, a random distribution or a specific pattern with each perforation having a predetermined position relative to other perforations. Perforations 33p, which can be any shape, for example, circular, have a cross-sectional area ranging between approximately 500 square-microns and 32 square-millimeters in the exemplary embodiment. Additionally, the exemplary embodiment limits the total surface area of perforations 10p to about 20 percent of the total area of foil 33.

The perforated-coil-etched foil can be made either by perforating a conventional core-etched foil or core-etching a perforated foil. Further details of the perforated core-etched foil are disclosed in co-pending U.S. patent application 09/165,779, entitled High-Energy Density Capacitors for Implantable Defibrillators. This application was filed on the same day as the present application and is incorporated herein by reference.

In addition to cathode 22 and three-part anode 24, FIG. 3 shows that capacitive assembly 21 includes thin electrolyte-impregnated separators 26, specifically 26a, 26b, 26c, and 26d. Separators 26a, 26b, 26c, and 26d, each of which consists of kraft paper impregnated with an electrolyte, such as an ethylene-glycol base combined with polyphosphates or ammonium pentaborate, distinguish in at least two ways from separators used in conventional electrolytic capacitors.

First, in contrast to conventional separators which are one-thousandth of an inch or more in thickness to improve fabrication yield and reduce electrolyte depletion, separators 26a–26d are each less than one-thousandth of an inch in thickness. In the exemplary embodiment, each of the separators has one of the following thicknesses: 0.000787, 0.0005 inches, and 0.00025 inches, with thicker papers preferably placed nearer the center of the active element to withstand the greater tensile stress that interior separators experience during winding.

However, various other embodiments of the invention use combinations of these thicknesses, combinations of these thickness with other thicknesses, and combinations of other thicknesses. Additionally, other embodiments of invention combine one or more thin separators with one or more conventional separators. Ultimately, the use of one or more thinner separators reduces the diameter of the active element for a given length of separator (assuming all other factors are equal).

Second, in contrast to conventional separators which are about four to six millimeters wider than the anode and cathode foils to provide large two to three millimeter end margins, separators 26 have a width 26w which is less than four millimeters wider than cathode 22 and anode 24 to provide smaller end margins 27a and 27b. For example, in the exemplary embodiment, width 26w is about 27 millimeters, or three millimeters wider than cathode 22 and anode 24, to provide end margins 27a and 27b of about 1.5 millimeters. Other embodiments of the invention provide at least one end margins of about 1.75, 1.25, 1, 0.75, 0.5, 0.25, and even 0.0 millimeters.

The large end margins of conventional separators are necessary to prevent damage to foil areas during high-speed fabrication and to insulate the cathode and anode foils from case 12. However, the inventors recognized that they are not necessary in all applications, particularly defibrillator applications, where high-speed fabrication is of little concern or where the inventors have devised other ways of insulating the foils from the top and bottom of aluminum case 12.

In particular, FIG. 2 shows that the exemplary embodiment provides two pairs of insulative inserts 30a–30b and 32a–32b, which prevent other conductive portions of capacitor 10, specifically anode tab 25 and rivets 15 and 17 and the interior surface of case 12, from shorting cathode 22 and anode 24. In the exemplary embodiment, these inserts are two pairs of paper disks, with each disk having a thickness of one one-thousandth of an inch and a diameter of about 14 millimeters. However, other embodiments of the invention use not only thinner or thicker inserts, but also different insert materials and numbers of inserts. For example, in one alternative embodiment, one or both pairs of inserts 30a–30b and 32a–32b consist of a polymeric insulator, and in another embodiment, inserts 30a and 30b consist of different material combinations, such as paper and a polymeric insulator.

Figure 5:
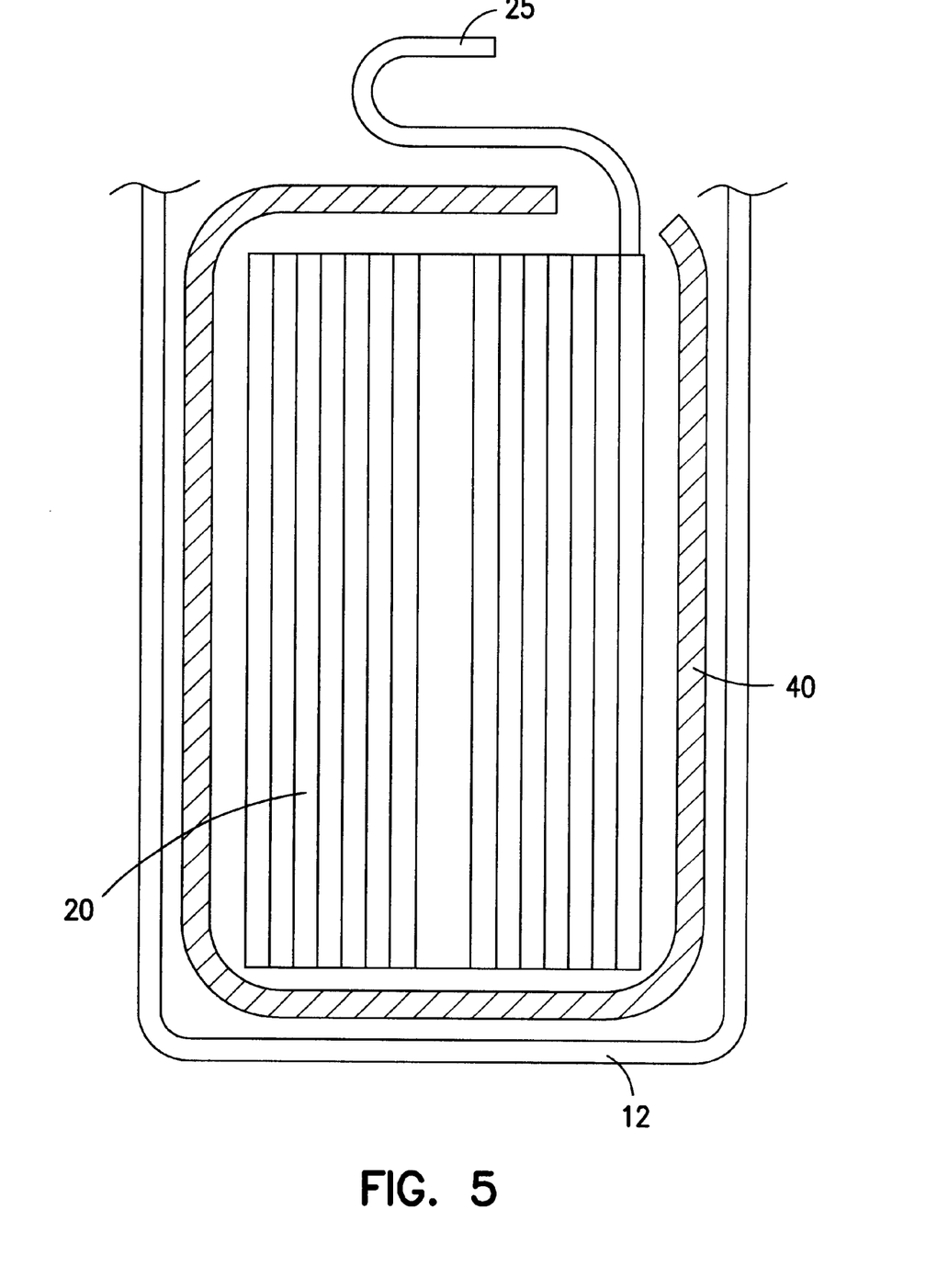
FIG. 5 is a partial cross-sectional view of an insulative bag 40 enclosing active element 20 in an alternative embodiment of capacitor 10.

As an alternative to insulative inserts, other embodiments enclose substantially all of active element 20 within an insulative bag. FIG. 5 shows an exemplary embodiment of an insulative bag 40 enclosing substantially all of active element 20, with the exception of the anode and cathode tabs. In this embodiment, bag 40 comprise materials similar to the insulative inserts.

FIG. 2 also shows that capacitive assembly 21 of active element 20 is wound around a mandrel (not shown), which has been removed after winding to leave an empty mandrel region or cavity 28. In this exemplary embodiment, mandrel region 28 has a width or diameter of about 2.5 millimeters, or more generally less than about 3.5 millimeters. In contrast to conventional electrolytic capacitors which have mandrels or mandrel regions with 3.5-millimeter diameters, the smaller mandrels of the present invention allow use of about 2–5 percent more aluminum foil without increasing the total volume of the capacitor. Another embodiment of the invention uses about the same amount of foil as conventional capacitors with the smaller mandrel region, thereby reducing the diameter of the active element without reducing energy density.

Mandrels with diameters less than 3.5 millimeters are not used in manufacturing conventional electrolytic capacitors primarily because they increase the difficulty in rolling the cathodes, anodes, and separators around them. Indeed, a smaller-diameter mandrel increases the tensile stress on the cathode, anode, and separators, leading them to break or tear during high-speed winding and thus to increase manufacturing waste. In addition, the smaller diameter mandrels tend to break and require replacement more often than larger mandrels. Thus, conventional capacitor manufactures avoid smaller mandrels to increase manufacturing yield and to accelerate manufacturing. However, these conventional objectives are of lesser importance when making small numbers of capacitors for implantable medical devices, specifically defibrillators.

EXEMPLARY EMBODIMENT OF IMPLANTABLE DEFIBRILLATOR

Figure 6:
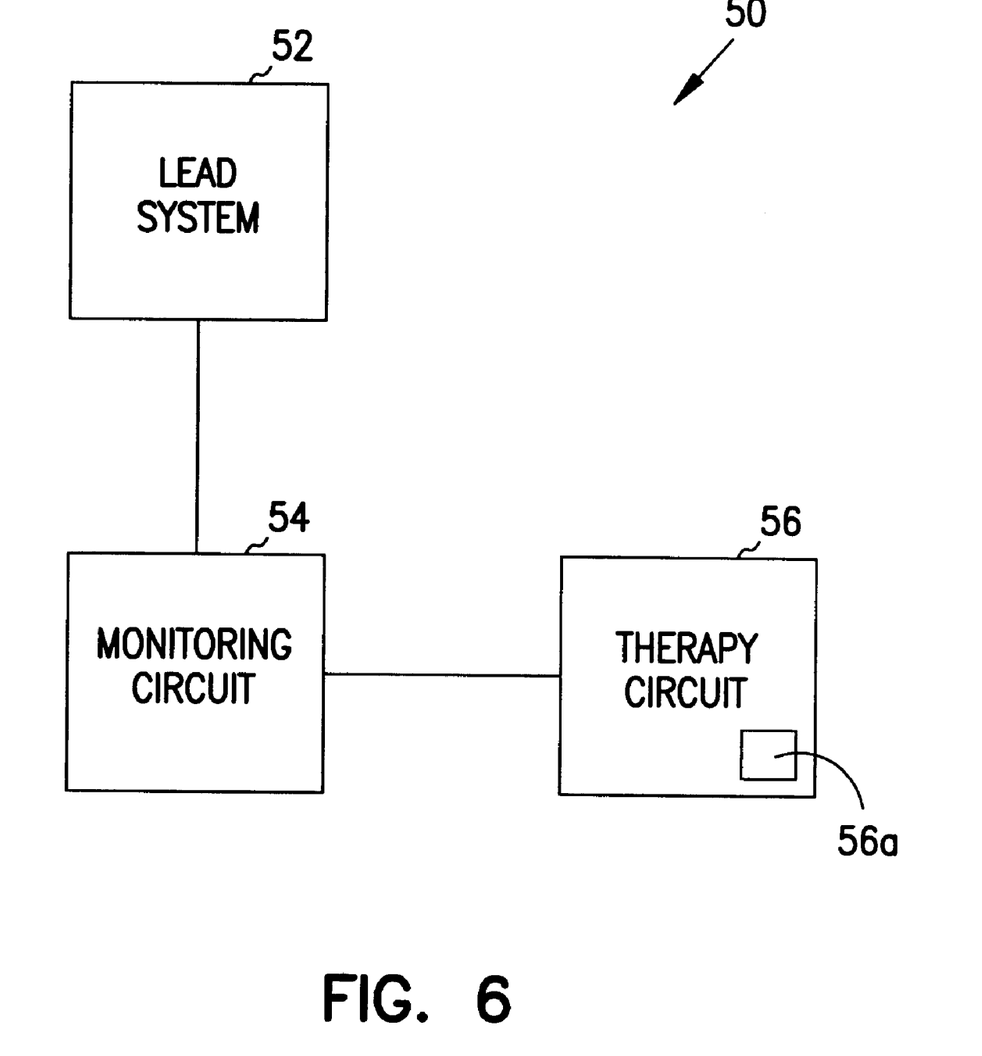
FIG. 6 is a block diagram of generic implantable defibrillator 50 including a capacitor that has one or more of the novel features of capacitor 10.

FIG. 6 shows one of the many applications for space-saving electrolytic capacitor 10: a generic implantable defibrillator 50. More specifically, defibrillator 50 includes a lead system 52, which after implantation electrically contacts strategic portions of a patient's heart, a monitoring circuit 54 for monitoring heart activity through one or more of the leads of lead system 52, and a therapy circuit 56 which delivers electrical energy through lead system 52 to the patient's heart. Therapy circuit 56 includes an energy storage component 56a which incorporates at least one capacitor having one or more of the novel features of capacitor 10. Defibrillator 50 operates according to well known and understood principles.

In addition to implantable defibrillators, the innovations of capacitor 10 can be incorporated into other cardiac rhythm management systems, such as heart pacers, combination pacer-defibrillators, and drug-delivery devices for diagnosing or treating cardiac arrhythmias. They can be incorporated also into non-medical applications, for example, photographic flash equipment. Indeed, the innovations of capacitor 10 are pertinent to any application where small, high energy, low equivalent-series-resistance (ERS) capacitors are desirable.

CONCLUSION

In furtherance of the art, the inventors have devised unique space-efficient packaging for aluminum electrolytic capacitors which allows either reduction of the actual size (total volume) of capacitors with specific electrical traits or improvement in the electrical traits of capacitors of a specific total volume. For example, in their exemplary embodiment, the inventors use thinner and narrower separators and top and bottom insulative inserts to achieve a capacitor which is about 33 percent smaller than conventional capacitors having similar electrical traits.

The embodiments described above are intended only to illustrate and teach one or more ways of practicing or implementing the present invention, not to restrict its breadth or scope. The actual scope of the invention, which embraces all ways of practicing or implementing the concepts and principles of the invention, is defined only by the following claims and their equivalents.

What is claimed is:

1. An implantable cardiac rhythm management system comprising:
   one or more leads for sensing electrical signals of a patient or for applying electrical energy to the patient;
   a monitoring circuit for monitoring heart activity of the patient through one or more of the leads; and
   a therapy circuit for delivering electrical energy through one or more of the leads to a heart of the patient, wherein the therapy circuit includes:
   at least one cylindrical electrolytic capacitor that has a nominal capacitance of at least 190 micro-farads, a voltage rating of at least 300 volts, and a total volume less than about 6 cubic-centimeters.

2. An implantable cardiac rhythm management system comprising:
   one or more leads for sensing electrical signals of a patient or for applying electrical energy to the patient;
   a monitoring circuit for monitoring heart activity of the patient through one or more of the leads; and
   a therapy circuit for delivering electrical energy through one or more of the leads to a heart of the patient, wherein the therapy circuit includes:
   at least one aluminum electrolytic capacitor comprising a cylindrical active element that includes a capacitive assembly having one or more separators and one or more foil members, with one or more of the separators having a width and one or more of the foil members having a width that is at most 3.5 millimeters less than the width of one or more of the separators; and
   at least one aluminum electrolytic capacitor comprising a cylindrical active element having a top and a bottom portion; a cylindrical case at least partly encasing the active element and having a bottom interior surface adjacent the bottom portion of the active element and an opening adjacent the top portion of the active element; a header positioned at least partly within the opening of the case; and one or more insulative inserts positioned between the top portion of the active element and the header or between the bottom interior surface of the case and the bottom portion of the active element.

3. The system of claim 2 wherein one or more of the separators has a nominal thickness of 0.000787, 0.0005, or 0.00025 inches and comprises paper and wherein the separators are impregnated with a non-polymer-based electrolyte.

4. The system of claim 2, wherein the one capacitor further includes: at least one foil that comprises:
   first and second opposing sides each having one or more of cavities having an average depth less than one-half the foil thickness; and two or more perforations through the foil.

5. The system of claim 4, wherein the average depth of the cavities is about one-third or one-fourth of the foil thickness.

6. The system of claim 4 wherein the average cross-sectional area of the perforations is about 2 to 100 times larger than the average cross-sectional area of the cavities.

7. The system of claim 4, wherein the one or more perforations include at least three perforations, wherein each of the perforations has an associated average maximum cross-sectional area between 500 square-microns and 32 square-millimeters, inclusive, and wherein at least one of the perforations has no alignment or mounting member extending through it.

8. An implantable cardiac rhythm management system comprising:
   one or more leads for sensing electrical signals of a patient or for applying electrical energy to the patient;
   a monitoring circuit for monitoring heart activity of the patient through one or more of the leads; and
   a therapy circuit for delivering electrical energy through one or more of the leads to a heart of the patient, wherein the therapy circuit includes one or more capacitors, with each capacitor including:
      one or more separators having a width;
      and one or more foil members having a width that is at most 3.5 millimeters less than the width of one or more of the separators, with each of the one or more foil members comprising
         first and second opposing sides each having one or more of cavities having an average depth less than one-half the foil thickness; and
         one or more perforations through the foil.

9. The system of claim 8 wherein the average depth of the cavities is about one-third or one-fourth of the foil thickness.

10. The system of claim 8 wherein the perforations have an average cross-sectional area larger than an average cross-sectional area of the cavities.

11. The system of claim 8 wherein the average cross-sectional area of the perforations is about 2 to 100 times larger than the average cross-sectional area of the cavities.

12. The system of claim 8, wherein the perforations include at least three perforations, wherein each of the perforations has an associated average maximum cross-sectional area between 500 square-microns and 32 square-millimeters, inclusive; and wherein at least one of the perforations has no alignment or mounting member extending through it.

13. An implantable cardiac rhythm management system comprising:
   one or more leads for sensing electrical signals of a patient or for applying electrical energy to the patient;
   a monitoring circuit for monitoring heart activity of the patient through one or more of the leads; and
   a therapy circuit for delivering electrical energy through one or more of the leads to a heart of the patient, wherein the therapy circuit includes one or more electrolytic capacitors comprising:
      a cylindrical active element having a top and a bottom portion, and including one or more foils each comprising:
         first and second opposing sides, with each side having one or more of cavities having an average depth less than one-half the foil thickness; and
         one or more perforations through the foil;
      a cylindrical case at least partly encasing the active element and having a bottom interior surface adjacent the bottom portion of the active element and an opening adjacent the top portion of the active element;
      a header positioned at least partly within the opening of the case; and
      one or more insulative inserts positioned between the top portion of the active element and the header or between the bottom interior surface of the case and the bottom portion of the active element.

14. The system of claim 13, wherein the one or more perforations include at least three perforations, wherein each of the perforations has an associated average maximum cross-sectional area between 500 square-microns and 32 square-millimeters, inclusive, and wherein each of the three perforations has no alignment or mounting member extending through it.

15. The system of claim 13, wherein the one or more perforations include at least three perforations, wherein each of the perforations has an associated average maximum cross-sectional area between 500 square-microns and 32 square-millimeters, inclusive, and wherein the three perforations are not colinear.

16. The system of claim 13 wherein the header has a thickness less than about 2.5 millimeters.

17. The system of claim 16 wherein the case includes a circumferential seating groove which has been partially or completely flattened to reduce case height.

18. The system of claim 16 wherein the cylindrical active element has a mandrel or mandrel region which has a width or diameter less than about 2.5 millimeters.

19. An implantable cardiac rhythm management system comprising:
   one or more leads for sensing electrical signals of a patient or for applying electrical energy to the patient;
   a monitoring circuit for monitoring heart activity of the patient through one or more of the leads; and
   a therapy circuit for delivering electrical energy through one or more of the leads to a heart of the patient, wherein the therapy circuit includes one or more cylindrical electrolytic capacitors comprising a cylindrical active element having a mandrel or mandrel region which has a width or diameter less than about 2.5 millimeters.

20. The system of claim 19, wherein each active element further comprises:
   one or more anode foils, with each anode foil comprising:
      first and second opposing sides each having one or more of cavities having an average depth less than one-half the foil thickness; and
      one or more perforations through the foil.

21. An implantable cardiac rhythm management system comprising:
   one or more leads for sensing electrical signals of a patient or for applying electrical energy to the patient;
   a monitoring circuit for monitoring heart activity of the patient through one or more of the leads; and
   a therapy circuit for delivering electrical energy through one or more of the leads to a heart of the patient, wherein the therapy circuit includes one or more capacitors, with each capacitor including:

one or more separators having a width;

and one or more foil members having a width that is at most 3.5 millimeters less than the width of one or more of the separators.

22. An implantable cardiac rhythm management system comprising:

one or more leads for sensing electrical signals of a patient or for applying electrical energy to the patient;

a monitoring circuit for monitoring heart activity of the patient through one or more of the leads; and a therapy circuit for delivering electrical energy through one or more of the leads to a heart of the patient, wherein the therapy circuit includes one or more capacitors, with each capacitor including:

one or more separators having a width;

and one or more foil members having a width that is at most 3.5 millimeters less than the width of one or more of the separators, with each of the one or more foil members comprising first and second opposing sides each having one or more of cavities having an average depth less than one-half the foil thickness; and means, including one or more perforations through the foil, for allowing flow of a liquid through the foil, with at least one of the perforations having no mounting member extending through it.

23. An implantable cardiac rhythm management system comprising:

one or more leads for sensing electrical signals of a patient or for applying electrical energy to the patient;

a monitoring circuit for monitoring heart activity of the patient through one or more of the leads; and a therapy circuit for delivering electrical energy through one or more of the leads to a heart of the patient, wherein the therapy circuit includes one or more capacitors, with each capacitor including:

one or more separators having a width;

and one or more foil members having a width that is at most 3.5 millimeters less than the width of one or more of the separators, with each of the one or more foil members comprising:

means, including one or more perforations through the foil, for allowing flow of a liquid through the foil, with at least one of the perforations having no mounting member extending through it;

first and second opposing surfaces; and means, between the first and second opposing surfaces, for enhancing durability of the foil.

* * * * *